US012611521B2

(12) United States Patent
Jang et al.

(10) Patent No.: US 12,611,521 B2
(45) Date of Patent: Apr. 28, 2026

(54) CATHETER SYSTEM

(71) Applicant: IUCF-HYU (INDUSTRY-UNIVERSITY COOPERATION FOUNDATION HANYANG UNIVERSITY), Seoul (KR)

(72) Inventors: Gun Hee Jang, Seoul (KR); Eun Soo Jung, Seoul (KR); Ji Min Park, Seoul (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 943 days.

(21) Appl. No.: 17/796,407

(22) PCT Filed: Jan. 25, 2021

(86) PCT No.: PCT/KR2021/000944
§ 371 (c)(1),
(2) Date: Jul. 29, 2022

(87) PCT Pub. No.: WO2021/153956
PCT Pub. Date: Aug. 5, 2021

(65) Prior Publication Data
US 2023/0050583 A1     Feb. 16, 2023

(30) Foreign Application Priority Data
Jan. 31, 2020     (KR) ........................ 10-2020-0012088

(51) Int. Cl.
A61M 25/01 (2006.01)
A61M 25/00 (2006.01)

(52) U.S. Cl.
CPC .... A61M 25/0127 (2013.01); A61M 25/0082 (2013.01); A61M 25/0116 (2013.01)

(58) Field of Classification Search
CPC .. A61B 2017/00477; A61B 17/320758; A61B 2017/320766; A61B 2017/320775;
(Continued)

(56) References Cited

U.S. PATENT DOCUMENTS

2007/0073247 A1*   3/2007   Ewaschuk .............. A61B 17/29
                                                              604/264
2008/0243106 A1*  10/2008   Coe ................... A61B 17/00234
                                                              606/1
(Continued)

FOREIGN PATENT DOCUMENTS

KR          10-1543708  B1      8/2015
KR          10-1749586  B1      6/2017
(Continued)

OTHER PUBLICATIONS

J. Park, et al., "Selective separating and assembling motion control for delivery and retrieval of an untethered magnetic robot in human blood vessels", AIP Advances, 2019, vol. 9, pp. 125136-1-125136-4 (4 pages total).
(Continued)

*Primary Examiner* — Thomas Mcevoy
(74) *Attorney, Agent, or Firm* — Sughrue Mion, PLLC

(57)          ABSTRACT
A catheter system is disclosed. A catheter system comprises a catheter module and a magnetic robot, which can be coupled to the catheter module, wherein: the catheter module comprises a catheter having an accommodation space formed on the front end thereof, and a rotational magnet that is rotatable; and the magnetic robot comprises a body and a magnet member, which is coupled to the body and induces magnetism with the rotational magnet.

7 Claims, 5 Drawing Sheets

10

(58) Field of Classification Search
CPC .......... A61B 34/73; A61B 2017/00876; A61B
17/1615; A61B 17/1617
See application file for complete search history.

(56) References Cited

U.S. PATENT DOCUMENTS

| | | |
|---|---|---|
| 2011/0144479 A1 | 6/2011 | Hastings et al. |
| 2019/0038370 A1 | 2/2019 | Weinberg et al. |

FOREIGN PATENT DOCUMENTS

| | | |
|---|---|---|
| KR | 10-1818400 B1 | 1/2018 |
| KR | 10-1831660 B1 | 2/2018 |
| KR | 10-1858904 B1 | 5/2018 |
| KR | 10-2018-0075550 A | 7/2018 |
| KR | 10-2042938 B1 | 11/2019 |
| WO | 2018/236104 A1 | 12/2018 |
| WO | 2019/022340 A1 | 1/2019 |
| WO | 2019/022380 A1 | 1/2019 |
| WO | 2019/031678 A1 | 2/2019 |

OTHER PUBLICATIONS

International Search Report for PCT/KR2021/000944, dated Jun. 10, 2021.

\* cited by examiner

[FIG.1]
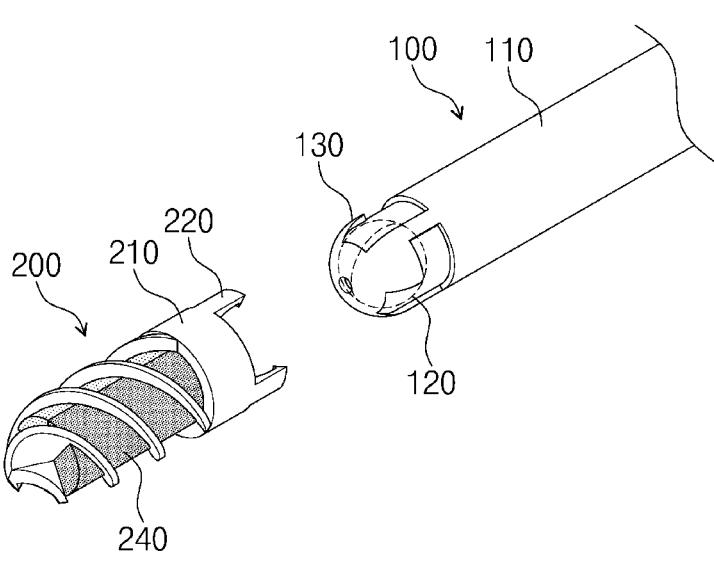
[FIG.2]
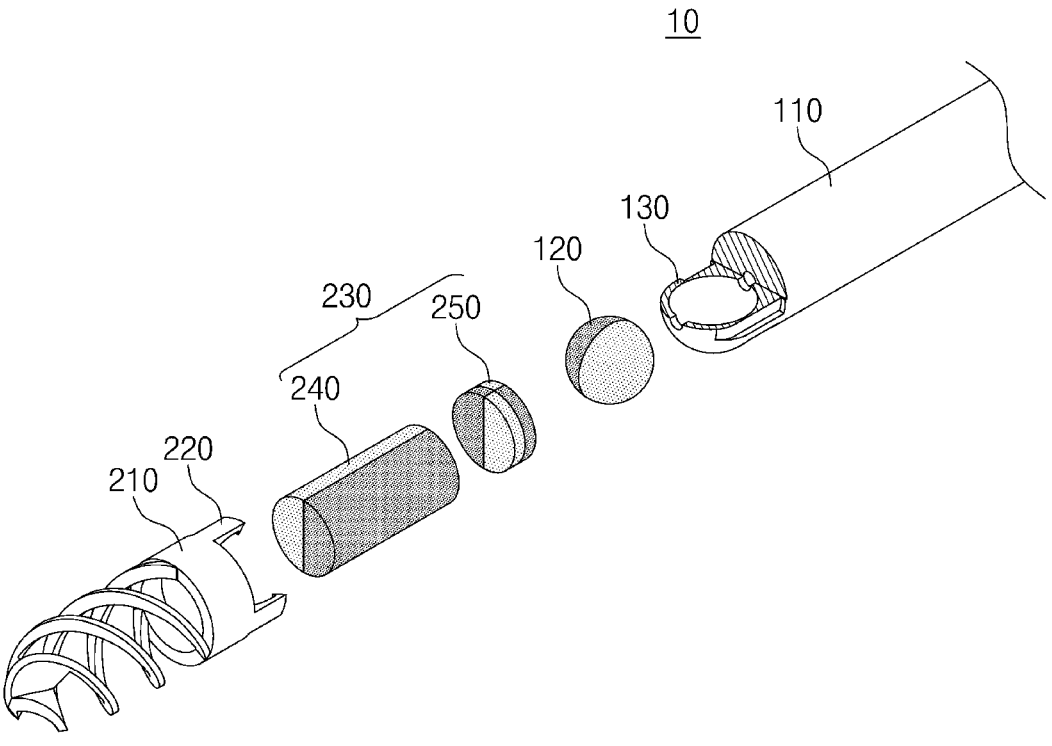

[FIG.3]
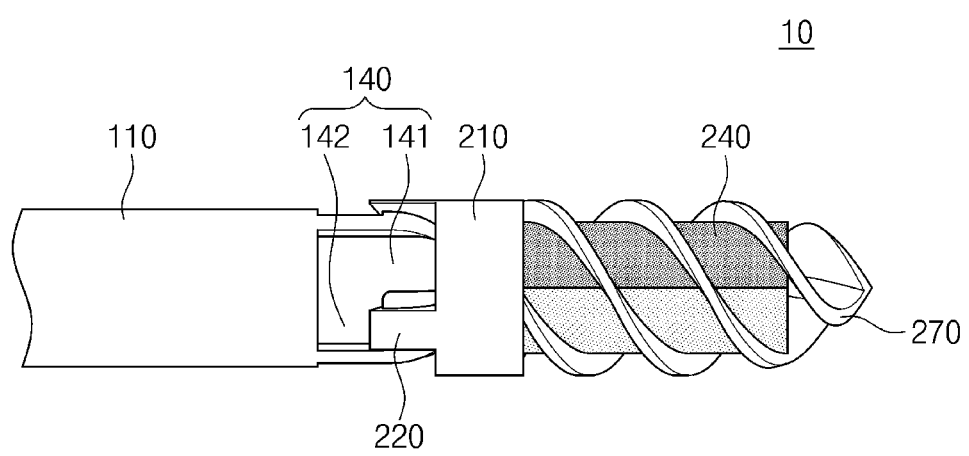
[FIG.4]
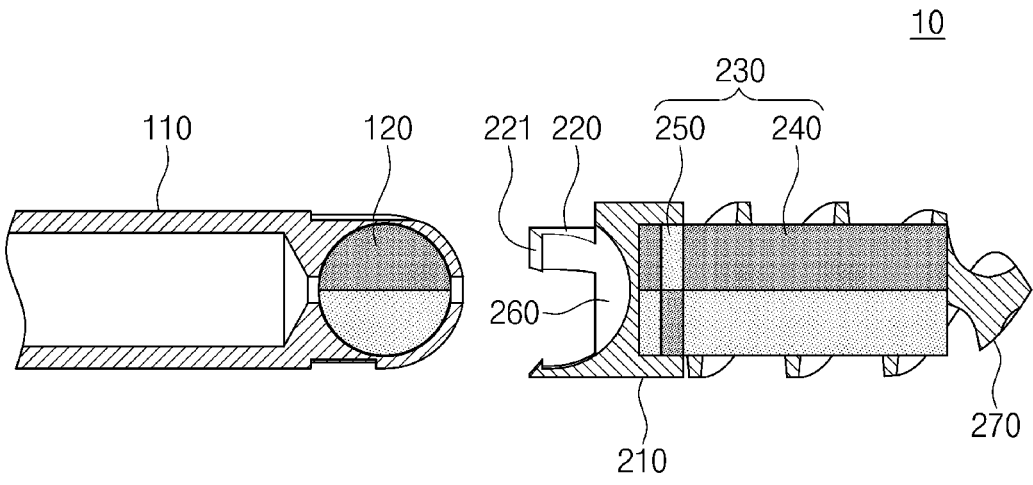

[FIG.5]
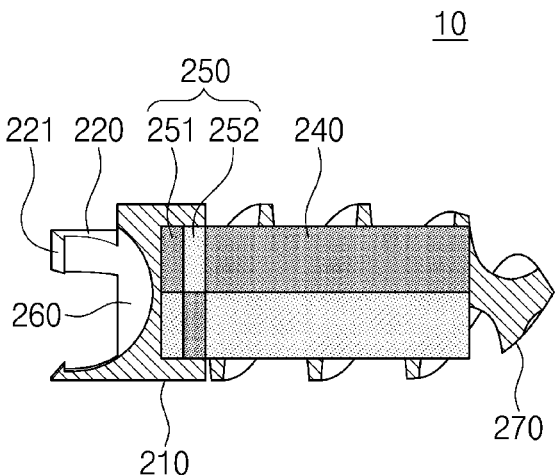
[FIG.6]
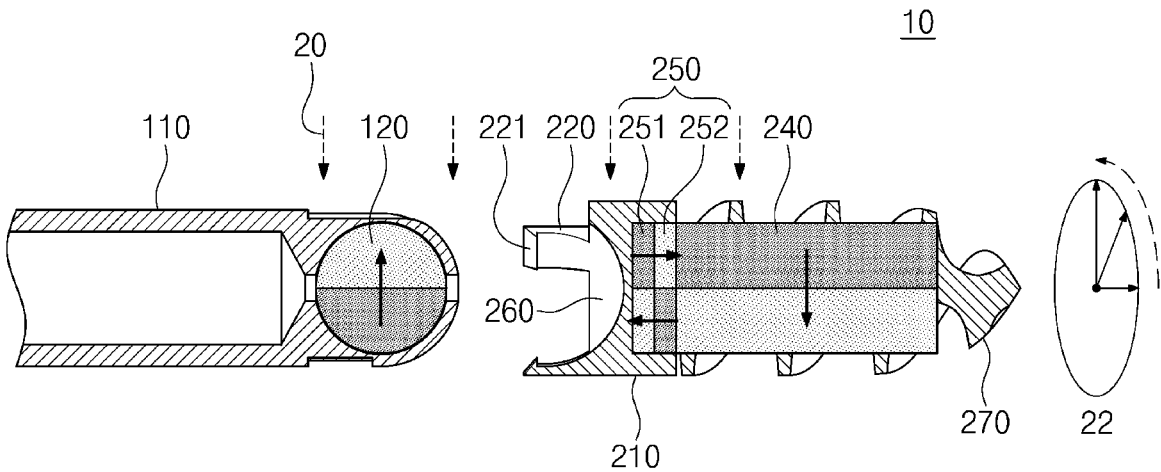

[FIG.7]
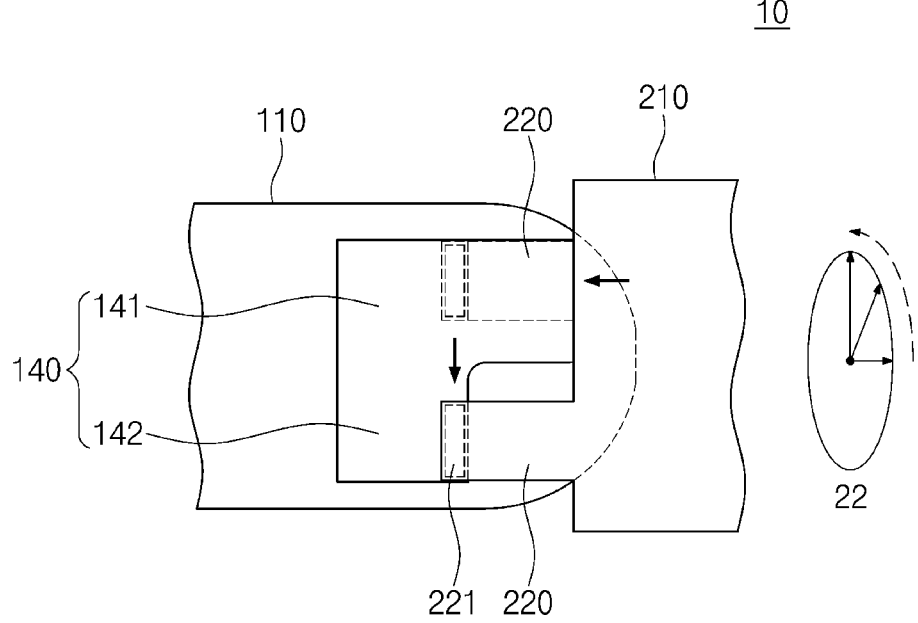
[FIG.8]
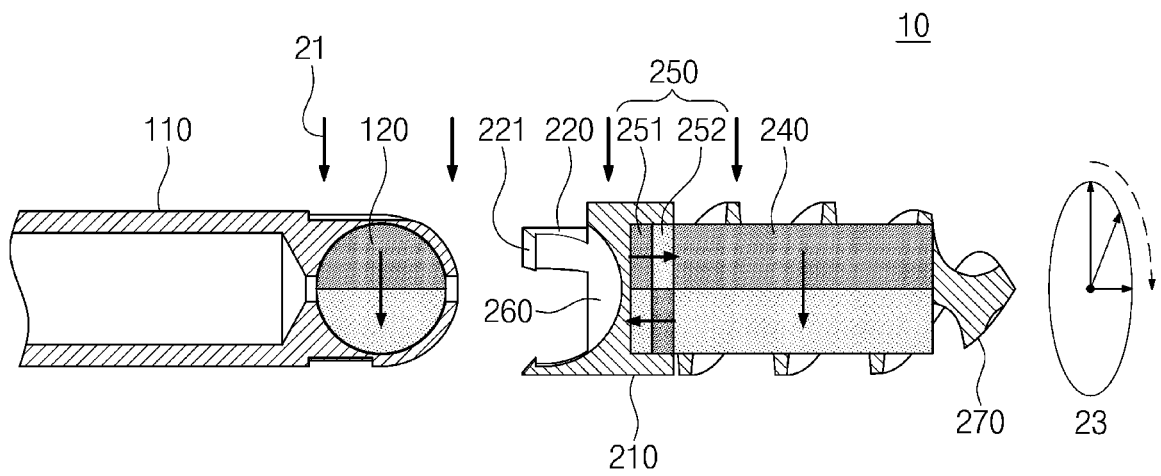

[FIG.9]
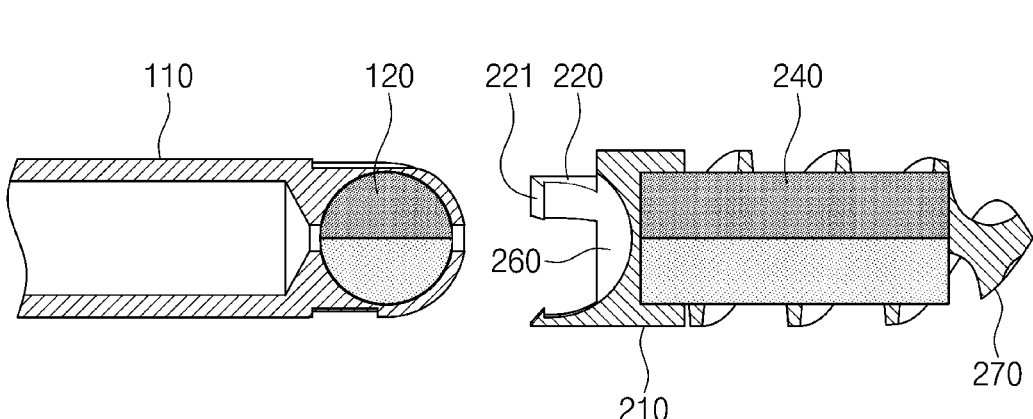
[FIG.10]
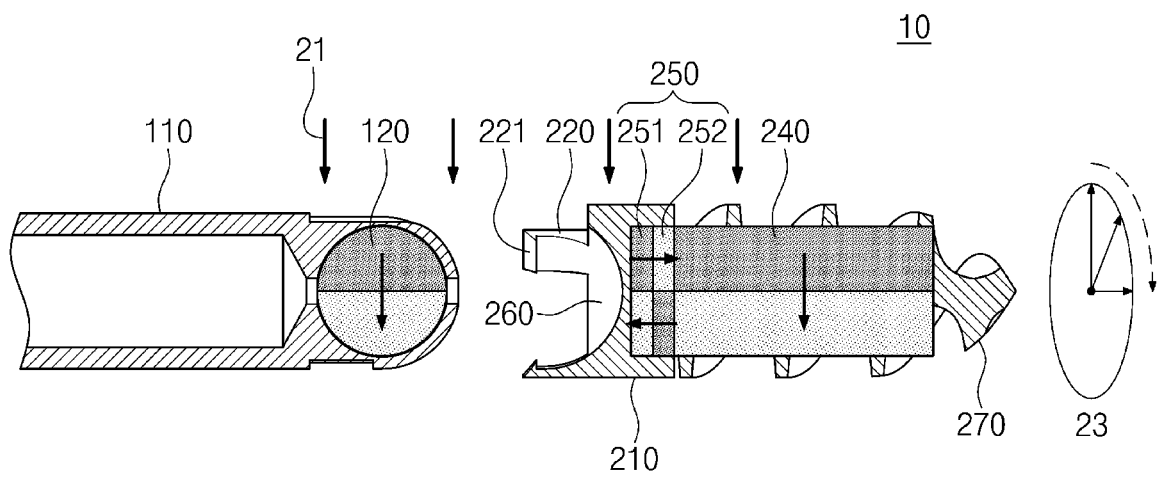

CATHETER SYSTEM

CROSS REFERENCE TO RELATED APPLICATIONS

This application is a National Stage of International Application No. PCT/KR2021/000944 filed Jan. 25, 2021, claiming priority based on Korean Patent Application No. 10-2020-0012088 filed Jan. 31, 2020.

TECHNICAL FIELD

The present invention relates to a catheter system, and more particularly, to a catheter system capable of separating and coupling a magnetic robot by using a catheter module.

BACKGROUND ART

In order to treat vascular diseases in a clogged or narrowed portion caused by angiostenosis due to thrombi and the like, it is common to perform coronary angioplasty through sequential processes of inserting a catheter through a femoral artery, widening a blood vessel with a manual operation of a doctor, and creating a device capable of maintaining the widened blood vessel. However, due to structural characteristics of the catheter, it may be difficult to apply the catheter to complex blood vessels, and the success of the procedure may greatly depend on the skill of the doctor.

While a conventional catheter system proposes a mechanism for coupling and separating a magnetic robot to and from a catheter tube by using magnetism, a repulsive force may act between a magnet fixed to the catheter tube and a magnet fixed to the magnetic robot depending on a position or a rotation angle of the magnetic robot, which may cause poor coupling. In addition, the magnetic robot may be pushed out or attached at an incorrect angle due to generation of the repulsive force, which may cause damage to blood vessels.

Accordingly, there is a demand for a catheter system in which a magnetic robot may be stably coupled regardless of a position, a posture, a rotation angle, and the like of the magnetic robot.

DISCLOSURE

Technical Problem

The present invention provides a catheter system in which a magnetic robot may be stably coupled regardless of a position, a posture, a rotation angle, and the like of the magnetic robot.

Technical Solution

According to the present invention, a catheter system includes: a catheter module; and a magnetic robot coupled to the catheter module, wherein the catheter module includes: a catheter having an accommodation space formed at a front end of the catheter; and a rotational magnet that is rotatable and located in the accommodation space, and the magnetic robot includes: a body; and a magnet member coupled to the body to induce magnetism with the rotational magnet.

In addition, the rotational magnet may have a spherical shape, and may be bisected into an N-pole and an S-pole.

In addition, the rotational magnet may have a cylindrical shape, and may be bisected into an N-pole and an S-pole based on a rotation axis.

In addition, the magnet member may include a driving magnet, and the driving magnet may have a cylindrical shape, and may be bisected into an N-pole and an S-pole based on a rotation axis.

In addition, the magnet member may further include a coupling magnet coupled to a rear end of the body on a rear side of the driving magnet, and the coupling magnet may include: a first magnet layer having a plate shape; and a second magnet layer having a plate shape, and facing the first magnet layer in an axial direction of the body, such that a polarity of the second magnet layer, which is opposite to a polarity of the first magnet layer, faces the polarity of the first magnet layer. The first magnet layer may have a same polarity area as the second magnet layer.

In addition, the body may include a coupling protrusion protruding rearward from a rear end of the body by a predetermined length, and a coupling groove into which the coupling protrusion is inserted may be formed in an outer peripheral surface of the front end of the catheter.

In addition, the coupling groove may include: a first region extending rearward from the front end of the catheter; and a second region extending perpendicularly to a longitudinal direction of the first region from a rear end of the first region.

Advantageous Effects

According to the present invention, the rotational magnet provided at the front end of the catheter may rotate so as to be aligned with an external magnetic field or the magnet member of the magnetic robot, so that the magnetic robot can be stably coupled to the catheter module regardless of a position, a posture, a rotation angle, and the like of the magnetic robot.

DESCRIPTION OF DRAWINGS

FIG. 1 is a perspective view showing a catheter system according to one embodiment of the present invention.

FIG. 2 is an exploded view showing the catheter system of FIG. 1 according to one embodiment of the present invention.

FIG. 3 is a view showing a coupling state of a catheter module and a magnetic robot of FIG. 1.

FIG. 4 is a sectional view showing a separation state of the catheter module and the magnetic robot of FIG. 1.

FIG. 5 is a sectional view showing the magnetic robot.

FIGS. 6 and 7 are views showing a process of coupling the catheter module to the magnetic robot according to one embodiment of the present invention.

FIG. 8 is a view showing a process of separating the catheter module from the magnetic robot according to one embodiment of the present invention.

FIG. 9 is a view showing a catheter system according to another embodiment of the present invention.

FIG. 10 is a view showing a catheter system according to still another embodiment of the present invention.

BEST MODE

According to the present invention, a catheter system includes: a catheter module; and a magnetic robot coupled to the catheter module, wherein the catheter module includes: a catheter having an accommodation space formed at a front end of the catheter; and a rotational magnet that is rotatable and located in the accommodation space, and the magnetic robot includes: a body; and a magnet member coupled to the body to induce magnetism with the rotational magnet.

Mode for Invention

Hereinafter, exemplary embodiments of the present invention will be described in detail with reference to the accompanying drawings. However, the technical idea of the present invention is not limited to the embodiments described herein, but may be realized in different forms. The embodiments introduced herein are provided to sufficiently deliver the idea of the present invention to those skilled in the art so that the disclosed contents may become thorough and complete.

When it is mentioned in the present disclosure that one element is on another element, it means that one element may be directly formed on another element, or a third element may be interposed between one element and another element. Further, in the drawings, thicknesses of films and regions are exaggerated for effective description of the technical contents.

In addition, in various embodiments of the present disclosure, the terms such as first, second, and third are used to describe various elements, but the elements are not limited by the terms. The terms are used only to distinguish one element from another element. Therefore, an element mentioned as a first element in one embodiment may be mentioned as a second element in another embodiment. The embodiments described and illustrated herein include their complementary embodiments. Further, the term "and/or" used herein is used to include at least one of the elements enumerated before and after the term.

As used herein, the terms of a singular form may include plural forms unless the context clearly indicates otherwise.

Further, the terms such as "including" and "having" are intended to designate the presence of features, numbers, steps, elements, or combinations thereof described in the present disclosure, and shall not be construed to preclude any possibility of the presence or addition of one or more other features, numbers, steps, elements, or combinations thereof. In addition, the term "connection" used herein is used to include both indirect and direct connection of a plurality of elements.

Further, in the following description of the present invention, detailed descriptions of known functions and configurations incorporated herein will be omitted when they may make the gist of the present invention unnecessarily unclear.

FIG. 1 is a perspective view showing a catheter system according to one embodiment of the present invention, FIG. 2 is an exploded view showing the catheter system of FIG. 1, FIG. 3 is a view showing a coupling state of a catheter module and a magnetic robot of FIG. 1, FIG. 4 is a sectional view showing a separation state of the catheter module and the magnetic robot of FIG. 1, and FIG. 5 is a sectional view showing the magnetic robot.

Referring to FIGS. 1 to 5, a catheter system 10 may include a catheter module 100, a magnetic robot 200, and a magnetic field generation unit (not shown).

The catheter module 100 may be coupled to and separated from the magnetic robot 200, and may deploy the magnetic robot 200 to the vicinity of a lesion while being coupled with the magnetic robot 200. The catheter module 100 may include a catheter 110 and a rotational magnet 120.

The catheter 110 may have a tube shape having a predetermined length, and may be inserted into a tubular tissue of a human body. The catheter 110 may be formed of a flexible material that is deformable.

An accommodation space 130 may be formed inside a front end of the catheter 110. The accommodation space 130 may have a shape corresponding to the rotational magnet 120.

A coupling groove 140 may be formed in an outer peripheral surface of the catheter 110. The coupling groove 140 may be formed at the front end of the catheter 110. The coupling groove 140 may include a first region 141 and a second region 142. The first region 141 may extend from the front end of the catheter 110 to a rear side of the catheter 110 by a predetermined length. The second region 142 may extend in a direction that is perpendicular to a longitudinal direction of the first region 141, and may communicate with the first region 141. According to an embodiment, the second region 142 may be formed in a circumferential direction of the catheter 110.

The rotational magnet 120 may be inserted into the accommodation space 130, and may rotate within the accommodation space 130 under the control of an external magnetic field 20. The rotational magnet 120 may rotate about a central axis thereof. The rotational magnet 120 may be bisected into an N-pole and an S-pole based on the central axis. According to one embodiment, the rotational magnet 120 may have a spherical shape. The magnetic robot 200 may be deployed to the vicinity of the lesion while being coupled to the catheter module 100, and may remove the lesion by moving under the control of the magnetic field generation unit while being separated from the catheter module 100.

The magnetic robot 200 may include a body 210 and a magnet member 230.

The body 210 may have a rod shape having a predetermined length, and may be formed of a non-magnetic material. The body 210 may be formed at a front end thereof with a drill tip 270, and formed on an outer peripheral surface thereof with a spiral protrusion. An inner space may be formed inside the body 210. In addition, the body 210 may be formed at a rear end thereof with a coupling protrusion 220 and a fastening groove 260.

The coupling protrusion 220 may protrude rearward from the rear end of the body 210 by a predetermined length. A latching part 221 may be formed at an end of the coupling protrusion 220. A plurality of coupling protrusions 220 may be formed.

The fastening groove 260 may be formed at the rear end of the body 210 to provide a space in which the front end of the catheter 110 is located when the catheter module 100 and the magnetic robot 200 are coupled to each other. The fastening groove 260 may have a shape corresponding to the front end of the catheter 110.

The magnet member 230 may be coupled to the body 210 to induce magnetism with the rotational magnet 120. The magnet member 230 may include a driving magnet 240 and a coupling magnet 250.

The driving magnet 240 may be inserted into the inner space of the body 210 so as to be fixedly coupled to the body 210. The driving magnet 240 may be driven integrally with the body 210. The driving magnet 240 may have a cylindrical shape, and may be bisected into an N-pole and an S-pole in an axial direction of the body 210.

The coupling magnet 250 may be inserted into the inner space on a rear side of the driving magnet 240. The coupling magnet 250 may be fixedly attached to a rear end of the driving magnet 240. The coupling magnet 250 may have a plate shape, and may have a diameter corresponding to a diameter of the driving magnet 240. The coupling magnet 250 may include a first magnet layer 251 and a second magnet layer 252.

The first magnet layer 251 may have a plate shape, and may be bisected into an N-pole and an S-pole based on an axis of the body 210. The second magnet layer 252 may have a plate shape, and may be bisected into an N-pole and an S-pole based on the axis of the body 210. The second magnet layer 252 may be configured such that a polarity of the second magnet layer 252, which is opposite to a polarity of the first magnet layer 251, faces the polarity of the first magnet layer 251. The first magnet layer 251 and the second magnet layer 252 may have the same polarity area. Accordingly, a magnetic moment value of the coupling magnet 250 may be zero, so that the coupling magnet 250 may not be affected by the external magnetic field 20.

The magnetic field generation unit may generate the external magnetic field 20. A direction of the external magnetic field 20 may be a direction that is perpendicular to a longitudinal direction of the catheter 110. In addition, the external magnetic field 20 may be a rotational magnetic field that rotates about a longitudinal axis of the catheter 110.

FIGS. 6 and 7 are views showing a process of coupling the catheter module to the magnetic robot according to one embodiment of the present invention, and FIG. 8 is a view showing a process of separating the catheter module from the magnetic robot according to one embodiment of the present invention.

Referring to FIGS. 6 and 7, the magnetic field generation unit may generate the first external magnetic field 20 in the direction that is perpendicular to the longitudinal direction of the catheter module 100. The first external magnetic field 20 may be controlled so that a magnetic force between the first external magnetic field 20 and the rotational magnet 120 may be weaker than a magnetic force between the rotational magnet 120 and the magnet member 230. Therefore, a magnetic field of the rotational magnet 120 may be aligned with a magnetic field of the coupling magnet 250, so that a polarity of the rotational magnet 120, which is different from the polarity of the first magnet layer 251, may face the polarity of the first magnet layer 251. In addition, an attractive force may act between the rotational magnet 120 and the coupling magnet 250 so that the magnetic robot 200 may move toward the catheter module 100. In this case, the coupling protrusion 220 may be inserted into the first region 141 of the coupling groove 140.

In addition, the magnetic field generation unit may generate a first rotating magnetic field 22 rotating about the longitudinal direction of the catheter module 100. The driving magnet 240 and the body 210 may rotate in a direction of the first rotating magnetic field 22, and the coupling protrusion 220 may be located in the second region of the coupling groove 140.

According to the process described above, the magnetic robot 200 may be coupled to the catheter module 100 by a magnetic force between the rotational magnet 120 and the coupling magnet 250 and by fastening of the coupling protrusion 220 and the coupling groove 140.

Referring to FIG. 8, the magnetic field generation unit may generate a second rotating magnetic field 23 in a reverse direction of the first rotating magnetic field 22. Due to the second rotating magnetic field 23, the driving magnet 240 and the body 210 may rotate in the reverse direction, and the coupling protrusion 220 may be located in the first region 141 of the coupling groove 140.

In addition, the magnetic field generation unit may generate the second external magnetic field 21 in the direction that is perpendicular to the longitudinal direction of the catheter module 100. The magnetic field generation unit may control the second external magnetic field 21 so that a magnetic force between the second external magnetic field 21 and the rotational magnet 120 may be stronger than the magnetic force between the rotational magnet 120 and the magnet member 230. Due to the second external magnetic field 21, the rotational magnet 120 and the driving magnet 240 may be aligned to match a magnetic field direction of the second external magnetic field 21. With such alignment, the rotational magnet 120 and the second magnet layer 252 may be aligned such that a polarity of the rotational magnet 120, which is the same as the polarity of the first magnet layer 251, may face the polarity of the first magnet layer 251, and a repulsive force may be generated between the rotational magnet 120 and the coupling magnet 250 so that the magnetic robot 200 may be pushed forward of the catheter module 100. In this process, the coupling protrusion 220 may be separated from the first region 141 of the coupling groove 140.

According to the process described above, the magnetic robot 200 may be separated from the catheter module 100. FIG. 9 is a view showing a catheter system according to another embodiment of the present invention.

Referring to FIG. 9, a magnet member 230 may include a driving magnet 240. The driving magnet 240 may have the same shape and diameter as the driving magnet 240 shown in FIG. 8. When a magnetic force between the first external magnetic field 20 and a rotational magnet 120 is weaker than a magnetic force between the rotational magnet 120 and the driving magnet 240, the rotational magnet 120 may be aligned with the driving magnet 240 by the magnetic field. Accordingly, an attractive force may act between the rotational magnet 120 and the driving magnet 240, so that the magnetic robot 200 may be coupled to the catheter module 100.

When the magnetic force between the first external magnetic field 20 and the rotational magnet 120 is stronger than the magnetic force between the rotational magnet 120 and the driving magnet 240, both the rotational magnet 120 and the driving magnet 240 may be aligned in a direction of the first external magnetic field 20, and a polarity of the rotational magnet 120, which is the same as a polarity of the driving magnet 240, may face the polarity of the driving magnet 240. Accordingly, a repulsive force may act between the rotational magnet 120 and the driving magnet 240, so that the magnetic robot 200 may be separated from the catheter module 100.

FIG. 10 is a view showing a catheter system according to still another embodiment of the present invention.

Referring to FIG. 10, a rotational magnet 120 may have a cylindrical shape. The rotational magnet 120 may be bisected into an N-pole and an S-pole based on a central axis, and may rotate about the central axis. The rotational magnet 120 may rotate about the central axis by a magnetic force with the second external magnetic field 21 or a magnet member 230.

Although the exemplary embodiments of the present invention have been described in detail above, the scope of the present invention is not limited to a specific embodiment, and should be interpreted by the appended claims. In addition, it should be understood by those of ordinary skill in the art that various changes and modifications can be made without departing from the scope of the present invention.

INDUSTRIAL APPLICABILITY

The catheter system according to the present invention may be used to remove a lesion within a tubular tissue of a human body.

The invention claimed is:

1. A catheter system comprising:
a catheter module; and
a magnetic robot coupled to the catheter module,
wherein the catheter module includes:
    a catheter having a spherical accommodation space formed at a hemispherical front end of the catheter; and
    a spherical rotational magnet that is capable of relative rotation with respect to the catheter by an external magnetic field and located in the spherical accommodation space, and
the magnetic robot includes:
    a body having a rear end formed with a fastening groove that has a shape corresponding to the hemispherical front end of the catheter; and
    a magnet member coupled to the body to induce magnetism with the spherical rotational magnet.

2. The catheter system of claim 1, wherein the spherical rotational magnet is bisected into an N-pole and an S-pole.

3. The catheter system of claim 1, wherein the magnet member includes a driving magnet, and the driving magnet has a cylindrical shape, and is bisected into an N-pole and an S-pole based on a rotation axis.

4. The catheter system of claim 3, wherein the magnet member further includes a coupling magnet coupled to the rear end of the body on a rear side of the driving magnet, and
the coupling magnet includes:
    a first magnet layer having a plate shape; and
    a second magnet layer having a plate shape, and facing the first magnet layer in an axial direction of the body, such that a polarity of the second magnet layer, which is opposite to a polarity of the first magnet layer, faces the polarity of the first magnet layer.

5. The catheter system of claim 4, wherein the first magnet layer has a same polarity area as the second magnet layer.

6. The catheter system of claim 1, wherein the body includes a coupling protrusion protruding rearward from the rear end of the body by a predetermined length, and
a coupling groove into which the coupling protrusion is inserted is formed in an outer peripheral surface of the hemispherical front end of the catheter.

7. The catheter system of claim 6, wherein the coupling groove includes:
    a first region extending rearward from the hemispherical front end of the catheter; and
    a second region extending perpendicularly to a longitudinal direction of the first region from a rear end of the first region.

* * * * *